United States Patent [19]

Blade et al.

[11] Patent Number: 5,162,367

[45] Date of Patent: Nov. 10, 1992

[54] PESTICIDAL COMPOUNDS

[75] Inventors: Robert J. Blade; John E. Robinson, both of Berkhamsted, England

[73] Assignee: The Wellcome Foundation Limited, Beckenham, United Kingdom

[21] Appl. No.: 426,509

[22] Filed: Oct. 23, 1989

Related U.S. Application Data

[63] Continuation of Ser. No. 123,331, Nov. 20, 1987, abandoned, which is a continuation-in-part of Ser. No. 52,551, May 20, 1987, abandoned, and a continuation-in-part of Ser. No. 96,855, Sep. 14, 1987, abandoned.

[30] Foreign Application Priority Data

May 21, 1986 [GB] United Kingdom ............... 8612391
Aug. 8, 1986 [GB] United Kingdom ............... 8619387

[51] Int. Cl.$^5$ .................. C07C 233/64; A01N 37/18
[52] U.S. Cl. .................... 514/465; 514/467; 514/521; 514/618; 514/622; 549/441; 549/452; 554/42; 554/45; 554/61; 554/62; 554/64; 554/65; 558/389; 564/162; 564/170; 564/172; 564/174
[58] Field of Search ............... 260/404; 549/452; 558/389; 564/162, 170, 172, 174; 514/465, 467, 521, 618, 622

[56] References Cited

U.S. PATENT DOCUMENTS

| | | | |
|---|---|---|---|
| 3,888,893 | 6/1975 | Siddall | 260/404 |
| 3,897,458 | 7/1975 | Diana et al. | 260/404 |
| 3,925,429 | 12/1975 | Schelling et al. | 260/404 |
| 3,932,483 | 1/1976 | Schelling et al. | 260/404 |
| 3,935,271 | 1/1976 | Schelling et al. | 260/404 |
| 4,713,200 | 12/1987 | Blade | 260/408 |
| 4,736,065 | 4/1988 | Elliot et al. | 260/404 |
| 4,855,086 | 8/1989 | Black et al. | 554/61 |

FOREIGN PATENT DOCUMENTS 57-212150 12/1982 Japan.

OTHER PUBLICATIONS

Miyakado et al., J. Pesticide Sci., 10, pp. 11-17 and 25-30 (1985).
CA 104 (23):202329r; Pesticidal Compounds, Wellcome Foundation, Ltd. (V).
CA (108)(3):21522k; Preparation of Alkeneamides and Thioalkene-amides as pesticides, Wellcome Foundation Ltd. (VI).
CA 108 (13):111994v; Preparation of 1-naphthoxyalkenamides as insecticides, Wellcome Foundation Ltd. (VII).
CA 106 (9):62876f; Search for new insecticidal and Fungicidal compounds from plants, Takarazuka Res. Cent. Sumitomo Chem. Co., Ltd. (VIII).
CA 103 (25):215014p; Pesticides, National Research Development Corp., (I).
CA 103(19):155782a The Piperacealamides, VIII Insecticidal activites of Phenoxy analogs of dehydropipercide, Takarazuka Res. Center, Sumitomo Chem. Co. (II).
CA 98 (21):178980f; Arylalkadienamides as insecticides and inticides; Sumitomo Chem. Co., Ltd. (III).
CA 102 (23):203678z; Synthesis of N-isobutyl-10-phenoxy, 2, 4 decadienamide; Fac Sci. Tech., Kinki Univ. (IV).

*Primary Examiner*—Bernard Dentz
*Attorney, Agent, or Firm*—Nixon & Vanderhye

[57] ABSTRACT

Insecticidal and acaricidal compounds of Formula $$AR(CH_2)_xO(CH_2)_mA(CH_2)_n(CE^1=CE^2)_a(CE^3=CE^4)CONR^1R^2 \quad (I)$$

wherein
Ar is phenyl or naphthyl, in either case optionally substituted by one or more of optionally substituted $C_{1-6}$ alkyl, optionally substituted $C_{1-6}$-alkylthio or $C_{1-6}$ alkylthiooxy, halogen or optionally substituted $C_{1-6}$ alkoxy,
x=0 or 1
m=1 to 7
n=1 to 7
A=$CH_2$ or oxygen
a=0 or 1
$R^1$ and $R^2$ are independently selected from hydrogen, $C_{1-6}$ alkyl and $C_{3-6}$ cycloalkyl (either of which may be substituted by one or more of halo, $C_{1-6}$ alkyl, $C_{2-6}$ alkenyl, $CF_{2-6}$ alkoxy, $C_{2-6}$ alkynyl, dioxalanyl and $C_{3-6}$ cycloalkyl)
$E^1$, $E^2$, $E^3$ and $E^4$ are independently selected from hydrogen, $C_{1-4}$ alkyl, optionally substituted by halo, and nitrile, provided that at least one of $E^1$, $E^2$, $E^3$ and $E^4$ is optionally substituted alkyl or nitrile provided that x is zero only when Ar is optionally substituted naphthyl.

12 Claims, No Drawings

PESTICIDAL COMPOUNDS

This is a continuation Ser. No. 123,331 filed on Nov. 20, 1988 (now abandoned), which is a continuation in part of Ser. No. 052,551, filed on May 20, 1987 (now abandoned) and a continuation in part of Ser. No. 096,855 filed on Sep. 14, 1987 (now abandoned).

FIELD OF THE INVENTION

This invention relates to pesticidal compounds.

BACKGROUND OF THE INVENTION

EP-A-164 187 (The Wellcome Foundation Limited) discloses pesticidal w-aryl lipid amide compounds having zero, one or two alkenyl links adjacent the carbonyl of the amide function, such links being optionally substituted by halo. It is stated that unsubstituted linking is preferred. It has now been found that surprisingly good activity is found when the unsaturated link is substituted by at least one optionally substituted alkyl group or nitrile group.

Miyakado et al (J. Pesticide Sci. 10, 25030, 1985) disclose various naturally-occurring and synthetic lipid amides, including two having a 3-methyl group, in other words a methyl group on the diene linking unit referred to above. However, except in the case of a compound having a 3,4-methylenedioxy substituent on the terminal aromatic group, they found that such a group did not increase insecticidal activity.

Japanese Patent Application No. 57/212 150 (Sumitomo) discloses w-benzyl and w-phenoxy dienamides, having an optional 3-methyl group, which are insecticidal and acaricidal.

BRIEF SUMMARY OF THE INVENTION

The present invention provides compounds of Formula (I)

$$Ar(CH_2)_xO(CH_2)_mA(CH_2)_n(CE^1=CE^2)_a(CE^3=CE^4)CONR^1R^2 \quad (I)$$

wherein

Ar is phenyl or naphthyl, in either case optionally substituted by one or more of $C_{1-6}$-alkyl, halogen, a group $RS(O)_z$— where R is $C_{1-4}$ alkyl optionally substituted by one or more halogen and z is 0, 1 or 2, $C_{1-6}$-alkoxy, $C_{1-6}$ alkyl substituted by one or more halogen, or $C_{1-6}$ alkoxy substituted by one or more halogen x=0 or 1
m=1 to 7
n=1 to 7
A=$CH_2$ or oxygen
a=0 or 1

$R^1$ and $R^2$ are independently selected from hydrogen, $C_{1-6}$ alkyl and $C_{3-6}$ cycloalkyl (either of which may be substituted by one or more of halogen, $C_{1-6}$ alkyl, $C_{2-6}$-alkenyl, $C_{2-6}$ alkoxy, $C_{2-6}$ alkynyl, dioxalanyl and $C_{3-6}$ cycloalkyl)

$E^1$, $E^2$, $E^3$ and $E^4$ are independently selected from hydrogen, $C_{1-4}$ alkyl optionally substituted by halogen, and nitrile, provided that at least one of $E^1$, $E^2$, $E^3$ and $E^4$ is optionally substituted alkyl or nitrile, provided that x is zero only when Ar is naphthyl or substituted naphthyl.

Preferably Ar is phenyl substituted by one or more halogen or trifluoromethyl groups. Conveniently, there are no more than three, preferably no more than two, such substituents. The entity constituted by halo-$C_{1-6}$ alkoxy substituted Ar may be a 2,2-difluoro-1,3-benzodioxol-5-yl group. The non-fluorinated analogue is not preferred.

Preferably a is 1. Suitably A is —$CH_2$— and the sum of m and n is equal to an odd number, preferably 3 or 5, or is equal to 6.

Preferably $R^1$ is hydrogen and $R^2$ is $C_{1-8}$ alkyl (most preferably isobutyl, 1,2-dimethylpropyl, 2,2-dimethylpropyl, 1,1,2-trimethylpropyl, or 1-methylpropyl) or dioxolanylalkyl such as (2-methyl-1,3-dioxalan-2-yl) methyl) or alkenylalkyl (such as 2-methylprop-2-enyl).

Preferably the stereochemistry of the or each double bond conjugated to the carbonyl is trans. Stereochemically pure compounds (I) are preferred. Although the presence of Z isomers maybe tolerated for reasons of economy, the content of such isomers is kept as low as possible, for example not exceeding 33%, 25%, 10% or 5%.

Suitably at least one of $E^1$, $E^2$, $E^3$ and $E^4$ is hydrogen and one other is methyl, fluoromethyl or trifluoromethyl. Preferably $E^1$, $E^2$ and $E^4$ are hydrogen and $E^3$ is methyl, fluoromethyl or trifluoromethyl, particularly methyl. N-isobutyl 11-(3,5-bistrifluoromethylbenzyloxy)-3-methylundeca-2,4-dienamide, N-isobutyl 12-(2-naphthyloxy)-3-methyldodeca-2,4-dienamide, N-isobutyl 11-(2,4-dichlorobenzyloxy)-3-methylundeca-2,4-dienamide and N-isobutyl 12-(3,5-bistrifluoromethylphenoxy)-3-methyldodeca-2,4-dienamide (in each case 2E, 4E) are particularly preferred compounds.

Thus, a particularly preferred class of compounds may be represented by Formula (IA):

$$Ar(CH_2)_xO(CH_2)_mCH_2(CH_2)_nCE^1=CH-CE^3=CH-CONHZ \quad (IA)$$

where: Ar is phenyl optionally substituted by 3,5-bistrifluoromethyl or 2,4-dichloro or 2,3,4,5,6-pentafluoro or Ar is 1-naphthyl or 2-naphthyl; x is 0 or 1 but is 0 only when Ar is naphthyl; $m+n=3$, 5 or 6; E1 and E3 are independently hydrogen or methyl but not both hydrogen; Z is isobutyl, 1,2-dimethyl, 2,2-dimethylpropyl or 1,1,2-trimethylpropyl; and the two double bonds are both E (i.e. trans), although the presence of some Z material may be tolerated for reasons of economy of manufacture.

Preferably, in Formula (IA), $E^1$ is hydrogen.

Compounds of Formula (I) may be prepared in any of the following ways:

(a) by amidation of the corresponding acid or acid derivative, i.e. by reaction of a compound of Formula (II) with a compound of Formula (III):

$$Ar(CH_2)_xO(CH_2)_mA(CH_2)_n(CE^1=CE^2)_a(CE^3=CE^4)COZ^1 \quad (II)$$

$$NHR^1R^2 \quad (III)$$

wherein $Z^1$ is hydroxyl, halo, a phosphoroimidate ester (-P(→0)(OAryl)NH.aryl) or alkoxy and the other variables are as defined above, (b) by reaction of a compound of Formula (IV) with a compound of Formula (V):

$$Ar(CH_2)_xO(CH_2)_mA(CH_2)_n(CE^1=CE^2)_pZ' \quad (IV)$$

$$Z''CONR^1R^2 \quad (V)$$

where one of Z' and Z'' is -C(O)$E^5$ and the other is $(Z^2)_3P=CE^6(CE^3=CE^4)_q$ or $(Z^2)_2P(O)=CE^6(-$ $CE^3=CE^4)_q$, wherein $Z^2$ is $C_{1-4}$ alkyl, $C_{1-4}$ alkoxy (preferably ethoxy) or aryl (preferably phenyl), p and q are each 0 or 1 and p+q is 0 or 1, and $E^5$ and $E^6$ are $E^1$, $E^2$, $E^3$ or $E^4$, as appropriate;

(c) by an elimination reaction on a compound of Formula (VI) or (VII)

$$Ar(CH_2)_xO(CH_2)_mA(CH_2)_n(CE^1=CE^2)CE^3(X)CE^4(Y)CONRR^2 \quad (VI)$$

$$Ar(CH_2)_xO(CH_2)_mA(CH_2)_nCE^1(X)CE^2(Y)CE^3=CE^4)CONR^1R^2 \quad (VII)$$

where one of X and Y is hydrogen and the other is a group $Q(\rightarrow O)L$, in which Q is sulphur or selenium and L is a suitable group such as $C_{1-4}$ alkyl (preferably methyl) or aryl (preferably phenyl);

(d) by reacting a compound of Formula (VIII) with a compound of Formula (IX):

$$Ar(CH_2)_xO(CH_2)_mA(CH_2)_nCE^1=CE^2-M \quad (VIII)$$

$$Hal-(CE^3=CE^4)CONR^1R^2 \quad (IX)$$

wherein Hal is halide e.g. bromide or iodide and M is a silicon-containing or metal-containing group, for example comprising zirconium, aluminium, zinc, tin, tellurium or copper, such as a bis-(cyclopentadienyl) zirconium chloride group, zirconium and zirconium-containing groups being generally preferred;

(e) by reaction of a compound of Formula (X) with a compound of Formula (XI):

$$Ar(CH_2)_xZ^3 \quad (X)$$

$$Z^4-(CH_2)_mA(CH_2)_n(CE^1=CE^2)_d(CE^3=CE^4)-CONR^1R^2 \quad (XI)$$

wherein one of $Z^3$ and $Z^4$ is —OH and the other is —OH or a suitable leaving group such as halo;

(f) when A is oxygen, by reaction of a compound of Formula (XII) with a compound of formula (XIII):

$$Ar(CH_2)_xO(CH_2)_mZ^5 \quad (XII)$$

$$Z^6-(CH_2)_n(CE^1=CE^2)_d(CE^3=CE^4)CONR^1R^2 \quad (XIII)$$

where one of $Z^5$ and $Z^6$ is —OH and the other is a suitable leaving group such as halo; or (g) by reacting a compound of Formula (XIV) with one of Formula (XV) or (where $E^3$ is H) with one of Formula (XVI):

$$Ar(CH_2)_xO(CH_2)_mA(CH_2)_nCE^1=CE^2-Hal \quad (XIV)$$

$$HCE^3=CE^4CONR^1R^2 \; {}^{(XVI)} \; E^3C=CE^4CONR^1R^2 \quad (XV)$$

where Hal is halogen, e.g. iodine or bromine, followed by semihydrogenation of the triple bond, if present.

(h) by conversion of one compound of Formula (I) prepared as above into another compound of Formula (I) by any suitable process.

Process (a) is normally carried out at 0° C. to room temperature (i.e. about 0°–25° or 0°–20° C.) in an aprotic solvent, such as ether, dichloromethane or benzene, optionally in the presence of a tertiary amine, such as triethylamine, but in the absence of water. If the compound of Formula (II) is an acid halide, for example acid chloride, then it may be formed from the corresponding acid by reaction with a suitable reagent such as oxalyl chloride or thionyl chloride. When $Z^1$ is a phosphoroimidate group then this is suitably formed from (PhO)P( O)NHPh Cl. The acid, or the acid function in the compound of Formula (II), may be prepared by hydrolysis of an ester, the ester being prepared by a conventional Wittig or Wadsworth-Emmons reaction, using for example an aldehyde and ethoxycarbonylmethylene triphenylphosphorane or an anion from triethylphosphonocrotonate. This latter reaction may result in an isomeric mixture, for example a mixture of (Z) and (E) substituted dienoates; such a mixture may be reacted as above, and the resulting mixture of amides separated by chromatography or other convenient techniques.

When $Z^1$ is alkoxy, the compound of Formula (II) is treated with a complex of the compound of Formula (III) and trialkyl (preferably trimethyl) aluminium in an aprotic solvent such as toluene, under reflux.

Alternatively, the ester referred to above may be derived by rearrangement and elimination on a compound of Formula (XIX)

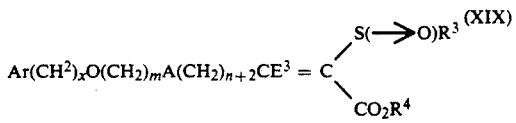

wherein $R^3$ is any suitable group, such as phenyl, and $R^4$ is $C_{1-4}$ alkyl, e.g. methyl or ethyl.

The compound of Formula (XIX) may be obtained by reaction of a compound of Formula (XX) with a compound of Formula (XXI):

$$Ar(CH_2)_xO(CH_2)_mA(CH_2)_{n+2}COH \quad (XX)$$

$$PhS(\rightarrow O)CH_2CO_2R^4 \quad (XXI)$$

A further route is for the ester above to be prepared by elimination on a compound of Formula (XXII):

$$Ar(CH_2)_xO(CH_2)_mA(CH_2)_n-A^1-A^2(CE^3=CE^4)-COOR^4 \quad (XXII)$$

wherein $R^4$ is as defined above, $A^1$ is —$CHE^1$— and $A^2$ is $CE^2(OR^5)$, $R^5$ being H or acyl such as acetyl. The reaction is preferably carried out in an aromatic solvent, conveniently in the presence of a molybdenum catalyst and a base, such as bis-trimethylsilylacetamide.

A further route for the above ester is by reaction of a compound of Formula (XXIII) with one of Formula (XXIV):

$$Ar(CH_2)_xO(CH_2)_mA(CH_2)_n(CE^1=CE^2)C(=O)E^3 \quad (XXIII)$$

$$Me_3SiCHE^4COOR^4 \quad (XXIV)$$

where $R^4$ is as above. This process may be carried out in a dry solvent, e.g. tetrahydrofuran in the absence of oxygen, in the presence of a base, e.g. lithium cyclohexylisopropylamide.

A further route for the above ester is by reaction of compound of Formula (XXV) with compound of Formula (XXVI)

$$Ar(CH_2)_xO(CH_2)_mA(CH_2)_n(CE^1=CE^2)BCO_2R^4 \quad (XXV)$$

$$E^3-M \quad (XXVI)$$

where B is a group —C(OD)=$CE^4$—, in which D is a suitable group such as dialkylphosphate or trifluoromethanesulphonate, M is a metal such as copper (I) or copper (I) associated with lithium or magnesium, and $R^4$ is as above.

This process can be performed at low temperature in a dry ethereal solvent such as diethyl ether, dimethyl sulphide or tetrahydrofuran in the absence of oxygen.

A still further route is for the ester to be formed by reaction of a compound of Formula (VIII) above with one of Formula (XXVII):

$$Hal—(CE^3=CE^4)CO_2R^4 \qquad (XXVII)$$

Process (b) is carried out in an anhydrous inert solvent, for example an ether such as tetrahydrofuran, optionally in the presence of a base, and preferably in the absence of oxygen, e.g. under a nitrogen atmosphere, at a low temperature ($-40°$ to $0°$ C.). The Wittig-type reagent may be obtained from compounds of Formula (V) by reaction with a base such as lithium diisopropylamide, butyllithium, sodium alkoxide or sodium hydride.

Process (c) may be effected by refluxing in a suitable non-polar solvent, such as benzene, toluene or xylene. The compound of Formula (VI) or (VII) may be prepared by oxidation, for example with periodate, of the corresponding compound having a QL group. This latter compound, in turn, may be prepared by reaction of a compound of Formula (XXVIII) with a compound of Formula (XXIX):

$$Ar(CH_2)_xO(CH_2)_mA(CH_2)_nCHE^1CE^2=CE^3G \qquad (XXVIII)$$

$$LS(\rightarrow O)CHE^4CONR^1R^2 \qquad (XXIX)$$

where G is an alkyl or aryl group. Preferably, the compound of Formula (XXIX) is reacted with trifluoroacetic anhydride in trifluoroacetic acid and then the compound of Formula (XXVIII) is added, at $0°-20°$ C.

Process (d) is normally carried out at room temperature, in a dry ethereal solvent such as tetrahydrofuran, in the presence of a palladium (0) catalyst, (such as bis(triphenylphosphine) palladium) and under an inert atmosphere of nitrogen or argon.

When processes (e) and (f) comprise the reaction of two alcohols, this is preferably in the presence of a dehydrating agent, such as concentrated sulphuric acid or diethyl diazo carboxylate, in a non-polar solvent at about $80-°110°$ C. When $Z^3$ is halo, a base is preferably present. Other standard methods for the formation of ethers and thioethers, such as those described in "Compendium of Organic Synthetic Methods", Harrison and Harrison, Wiley Interscience, (New York) 1971, may be used.

Process (g) may be conducted at room temperature to reflux in the presence of a base, e.g. triethylamine and a palladium (o) catalyst in the absence of oxygen.

The alkyne compound of Formula (XVII) or (XVIII) may, when $E^1$ or $E^3$ is hydrogen, be prepared by reaction of a compound of Formula (XXX) with a compound of Formula (XXI) or (XXXII):

$$Ar(CH_2)_xO(CH_2)_mA(CH_2)_n—Hal \qquad (XXX)$$

$$E^1C\equiv C(CE^3=CE^4)CONR^1R^2 \qquad (XXXI)$$

$$E^3C\equiv C—CONR^1R^2 \qquad (XXXII)$$

at room temperature or lower, in the presence of a base such as butyl lithium) and in an etheral solvent (such as THF) or by any process analogous to processes (a) to (h) above, resulting in the formation of a compound having a triple bond.

The intermediates of Formula (III)–(XXXII) may be prepared by standard methods. For example, the compounds of Formula (V) may be prepared by the reaction of an appropriate phosphine, phosphonate or phosphite with an w-halo amide.

Compounds of Formula (IV) may be prepared by hydrolysis of a ketal ring or oxidation of the corresponding alcohol, for example using pyridinium chlorochromate or oxalyl chloride/DMSO.

Compounds of Formula (I) may be used to control arthropod pests such as insects and acarines. Acaricidal activity has been found to be enhanced when $R^1$ is hydrogen and $R^2$ has an alkyl substituent alpha to the nitrogen, for example when $R^2$ is 1,2-dimethylpropyl.

The compounds of Formula (I) may be used for such purposes by application of the compounds themselves or in diluted form in known fashion as a dip, spray, lacquer, foam, dust, powder, aqueous suspension, paste, gel, shampoo, grease, combustible solid, vapour emanator (e.g. coil, mat or the like), granule, aerosol, oil suspensions, oil solutions, pressure-pack, impregnated article (such as a plastics ear tag or collar or a strip to treat the air of an enclosed space) or pour-on formulation. Dip concentrates are not applied per se, but diluted with water and the animals immersed in a dipping bath containing the dip wash. Sprays may be applied by hand or by means of a spray race or arch. The animal, plant or surface may be saturated with the spray by means of high volume application or superficially coated with the spray by means of light or ultra low volume application. Aqueous suspensions may be applied to the animal in the same manner as sprays or dips. Dusts may be distributed over the animals by means of a powder applicator or incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of Formula (I) may be formulated either as formulations ready for use on the animals or as formulations requiring dilution prior to application, but both types of formulation comprise a compound of Formula (I) in intimate admixture with one or more carriers or diluents. The carriers may be liquid, solid or gaseous or comprise mixtures of such substances, and the compound or Formula (I) may be present in a concentration of from 0.025 to 99% w/v depending upon whether the formulation requires further dilution.

Dusts, powders and granules comprise the compound of Formula (I) in intimate admixture with a powdered solid inert carrier for example suitable clays, kaolin, talc, mica, chalk, gypsum, vegetable carriers, starch and diatomaceous earths.

Sprays of compound of Formula (I) may comprise a solution in an organic solvent (e.g. those listed below) or an emulsion in water (dip wash or spray wash) prepared in the field from an emulsifiable concentrate (otherwise known as a water miscible oil), a wettable powder or a controlled release formulation, such as a microencapsulated formulation. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use. Microencapsulated formulations may be made by any known technique, for example coacervation or interfacial polymerisation.

Lacquers comprise a solution of the active ingredient in an organic solvent, together with a resin, an optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. Aqueous solutions may also be formed from acid addition salts of a compound of Formula (I). The suspensions or solutions may be applied per se or in a diluted form in known fashion. Electrostatic spraying techniques may be used with suitable formulations.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as a uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium which also contains a viscous oil to minimise spreading of the formulation on the surface of the animals. An avian or mammal host may also be protected against infestation of acarine ectoparasites by means of carrying a suitably-moulded, shaped plastics article impregnated with a compound of Formula (1). Such articles include impregnated collars, tags, bands, sheets and strips suitably attached to appropriate parts of the body.

The concentration of the compound of Formula (I) to be applied to a locus (e.g. animal, grain, crop, soil, building etc.) will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation, but in general will lie in the range from 0.0001% to 0.5% except for undiluted formulations such as pour-on formulations which in general will be deposited at a concentration in the range from 0.1 to 20.0% and preferably 0.1 to 10%. For public health usage, a deposited concentration of up to about 5% may be needed. The concentrate may contain up to 90% active ingredient.

Dusts, greases, pastes and aerosol formulations are usually applied in a random fashion as described above and concentrations of 0.001 to 20% w/v of a compound of Formula (I) in the applied formulation may be used.

Bait formulations for, for example, cockroaches will include suitable attractants and/or foodstuffs. The compounds of the invention can be formulated specifically for use on grain or on the exposed surfaces of buildings, or for space spraying.

The compounds may be administered in an animal's feed to combat insect larvae infesting the animal's dung. Any suitable formulation, including microencapsulated material, may be used. The amount of the compound which is administered will vary according to the type and size of animal, and is chosen to provide a suitable concentration of the compounds in the animal's dung. Typically, 0.001 to 100 mg/kg bodyweight, preferably 0.1 to 10 mg/kg, are administered daily, to give concentrations of 0.001 to 1%, preferably 0.01 to 0.1% compound in the dung. The compound will usually be formulated as a concentrate or premix for mixing with a feed supplement, feed concentrate, roughage or the like. Alternatively, the compound may be added to the supply of drinking water. Suitable animals include cattle, pigs, horses, sheep, goats and poultry.

Insect pests include members of the orders Coleoptera (e.g. Anobium, Tribolium, Sitophilus, Diabrotica, Anthonomus, Hylotrupes or Anthrenus spp.), Lepidoptera (e.g. Ephestia, Plutella, Chilo, Heliothis, Spodoptera, Tinea or Tineola spp.), Diptera (e.g. Anopheles, Simulium, Musca, Aedes, Culex, Glossina, Stomoxys, Haematobia, Tabanus, Hydrotaea, Lucilia, Chrysomia, Callitroga, Dermatobia, Hypoderma, Liriomyza, and Melophagus spp.), Phthiraptera (Malophaga e.g. Damalina spp. and Anoplura e.g. Linognathus and Haematopinus spp.) Hemiptera (e.g. Triatoma, Rhodnius, Aphis, Bemisia, Aleurodes, Nilopavata, Nephrotetix or Cimex spp.), Orthoptera (e.g. Schistocerca or Acheta spp.), Dictyoptera (e.g. Blattella, Periplaneta or Blatta spp.), Hymenoptera (e.g. Solenopsis or Monomorium spp.), Isoptera (e.g. Reticulitermes spp.), Siphonaptera (e.g. Ctenocephaliues or Pulex spp.), Thysanura (e.g. Lepisma spp.), Dermaptera (e.g. Forficula spp.) and Psocoptera (e.g. Peripsocus spp.). Acarine pests include ticks, e.g. members or the genera Boophilus, Rhipicephalus, Amblyomma, Hyalomma, Ixodes, Haemaphysalis, Dermocentor and Anocentor, and mites and manges such as Tetranychus, Psoroptes, Psorergates, Chorioptes, Demodex, Dermatophagoides, Acarus, Tyrophagus and Glycyphagus Spp.

The compounds exhibit killing and/or knockdown activity against adult and/or larval arthropod pests.

Compounds of the invention may be combined with one or more other active ingredients (for example pyrethroids, carbamates and organophosphates) and/or with attractants and the like. Furthermore, it has been found that the activity of the compounds of the invention may be enhanced by the addition of a synergist or potentiator, for example one of the oxidase inhibitor class of synergists, such as piperonyl butoxide or NIA 16388. When an oxidase inhibitor synergist is present in a formula of the invention, the ratio of synergist to compound of Formula (I) will be in the range 25:1-1:25 e.g. about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin).

It will be understood that what we will claim may comprise:

(a) compounds of Formula (I);
(b) processes for the preparation of compounds of Formula (I);
(c) insecticidal and acaricidal compositions comprising a compound of Formula (I) in admixture with a carrier;
(d) processes for the preparation of such pesticidal compositions;
(e) methods for the control of insect or acarine pests comprising the application to the pest or its environment of a compound of Formula (I);
(f) synergised pesticidal compositions comprising a compound of Formula (I);
(g) potentiating or non-potentiating mixtures of a compound of Formula (I) and another pesticidal compound; and
(h) novel intermediates of the preparation of compounds of Formula (I), particularly compounds of Formula (II).

The following Examples illustrate, in a non-limiting manner, preferred aspects of the invention. All temperatures are in degrees Celsius.

EXAMPLE 1

Triethyl-4-phosphono-3-methylcrotonate

A mixture of ethyl 3,3-dimethylacrylate (12.8g, 100 mmol), N-bromosuccinimide (11.8g, 66 mmol), dry benzene (50 ml) and benzoyl peroxide (20 mg) was heated under reflux for 0.5h. After cooling, filtration, concentration and distillation, ethyl 4-bromo-3-methylcrotonate was obtained. The latter (33.8 mmol) was added dropwise to triethylphosphite (47.17 mmol) at 100°. The mixture was warmed to 150o and the residue purified by distillation to give triethyl 4-phosphono-3-methylcrotonate (b.p. 120° at 0.5 mm.Hg) as a cis/trans mixture.

EXAMPLE 2

N-Isobutyl 11-(3',5'-bistrifluoromethylbenzyloxy)-3-methylundeca-2,4-dienamide 7-(3',5'-bistrifluoromethylbenzyloxy)-heptan-1-al (4.7g, 13.27 mmol) (prepared according to methods described in U.S. Pat. No. 4,713,200 was reacted with the anion derived from the compound of Example 1 (13.27 mmol) and lithium diisopropylamide (13.27 mmol) in dry tetrahydrofuran in the absence of moisture from −40° to room temperature. After standard workup and purification on column chromatography (silica/85:15 hexane:ether), ethyl 11-(3',5'-bistrifluoromethylbenzyloxy)-3-methyl-undeca-2, 4-dienoate was obtained.

The above ester (10.2 mmol) was hydrolysed by potassium hydroxide (41.2 mmol) in aqueous ethanol at room temperature over 24 hours. After standard workup, the residue was triturated with hexane to give ( 2E,4E) 11-(3',5'-bistrifluoromethylbenzyloxy)-3-methylundeca-2, 4-dienoic acid.

The above acid (0.5 mmol) was treated sequentially with triethylamine (0.5 mmol) and phenyl N-phenylphosphoramidochloridate (0.5 mmol) in dichloromethane in the absence of moisture. After 30 mins, triethylamine (0.5 mmol) and isobutylamine (0.5 mmol) were added sequentially and after 16 hours at room temperature the reaction was worked up in standard fashion. The crude material was purified by flash column chromatography (silica/80:20 ether:hexane) to give (2E,4E) N-isobutyl-11-(3',5'-bistrifluoromethylbenzyloxy)-3-methylundeca-2, 4-dienamide as a pale yellow oil. Glc, 3% OV210 at 250°, retention time 2.9 min; tlc, $R_f$(silica-ether) 0.58; NMR; 7.61 ppm (3H), S, aromatic; 5.81, (3H), 4,H5,NH;5.49, (1H),S,H2; 4.42,(2H), S, benzylic $CH_2$; 3.44,(2H), t,H11; 2.20, (3H), S(bd), Me; 2.22,(3H),m, H6,$Bu^i$; 1.37, (8H),m,H7,8,9,10;3.20,(2H),d of d; 0.94,(6H),d,$Bu^i$.

The following compounds, all (2E, 4E) unless otherwise stated, were prepared similarly:

EXAMPLE 3

N-2,2-Dimethylpropyl 11-(3',5'-bistrifluoromethylbenzyloxy)-3-methylundeca-2,4-dienamide tlc; $R_f$(silica-ether) 0.52

EXAMPLE 4

N-1-methylpropyl 11-(3',5'-bistrifluoromethylbenzyloxy)-3-methyl-2,4-dienamide tlc, $R_f$(silica-ether) 0.43.

EXAMPLE 5

N-1,2-dimethylpropyl 11-(3',5'-bistrifluoromethylbenzyloxy)-3-methylundeca-2,4-dienamide.

Trimethylaluminium (4.2 mmol) in dry toluene was treated with 1,2-dimethylpropylamine (4.2 mmol) at −10°. After 30 mins (0°→room temp) the ester of Example 1 (3.82 mmol) in toluene was added. The mixture was heated under reflux for 6h in the absence of moisture and oxygen, treated with aqueous hydrochloric acid and worked up in standard fashion. The crude material was purified (silica/1:1 ether:hexane) by column chromatography to give (2E/Z,4E) N-1,2-dimethylpropyl 11-(3',5'-bistrifluoromethylbenzyloxy)-3-methylundeca-2,4-dienamide as a pale yellow oil. (85:15 2E,4E:2Z,4E). Glc; OV210 at 250°, $R_t$ 2.2,1.5 mins; tlc, silica-ether, $R_f$0.60.

EXAMPLE 6

N-isobutyl 11-(3,5-bistrifluoromethylbenzyloxy)-5-methyl-undeca-2,4-dienamide 7-(3',5')-(Bistrifluoromethylbenzyloxy)-heptan-1-al (26.5 mmol) was reacted in dry ether with methyl magnesium iodide (26.5 mmol) and worked up in conventional fashion. The crude material was purified by column chromatography to give 8-(3',5'-bistrifluoromethylbenzyloxy)-octan-2-ol.

The above alcohol (16.17 mmol) was oxidised using methods described in EP-A-164 187 (Swern oxidation, DMSO, oxalyl chloride, triethylamine) to give 8-(3',5'-bistrifluoromethylbenzyloxy)-octan-2-one. The ketone was reacted with triethyl-4-phosphonocrotonate/lithium diisopropylamide to give ethyl 11-(3',5'-bistrifluoromethyl)benzyloxy- 5-methylundeca-2,4-dienoate. The ester was converted into the amide as in Example 5.

The product was purified by preparative reverse phase HPLC (85% methanol—15% water) to give (2E,4E)N-isobutyl 11-(3',5'-bistrifluoromethylbenzyloxy)-5-methylundeca-2,4-dienamide as a yellow oil. Glc; OV210 at 270° $R_t$ 6.2 mins; tlc, silica-ether, $R_f$ 0.48, NMR; 7.75,(3H), S,aryl; 7.52, (1H),d of u, H3; 5.95, (1H),d,H4; 5.85,(1H), NH; 5.75, (1H),d,H2; 4.56, (2H), S, benzylic; 3,52,(2H),t,H11; 2.12, (2H),t,H6; 1.65-1.3,(8H),H7,8,9, 10; 1.85, (3H),S,Me; 3.16,(2H),d of d, 1.8,(1H),m,0.91, (6H),d,isobutyl.

EXAMPLE 7

(2E, 4E) N-1,2-dimethylpropyl 11-(3',5'-bistrifluoromethylbenzyloxy) 5-methyl-undeca-2,4-dienamide The compound was prepared as in Example 6. tlc, silica-ether $R_f$ 0.52.

EXAMPLE 8

(2E, 4E) N-isobutyl 11-(3',5')-bistrifluoromethylbenzyloxy)-3,5-dimethylundeca-2,4-dienamide 8-(3',5'-bistrifluoromethylbenzyloxy)octan-2-one was reacted with triethyl 4-phosphono-3-methylcrotonate/-lithium diisopropylamide to give an ester which was converted as in Example 5 into (2E,4E) N-isobutyl 11-(3',5'-bistrifluoromethylbenzyloxy)-3,5-dimethylundeca-2,4-dienamide. Pale yellow oil, tlc (silica-ether) $R_f$ 0.59; NMR; 7,80,(3H),S,aryl; 5.69, (1H),S,H4; 5.54, (1H),S,H2; 4.60, (2H), S, benzylic, 3.54, (2H), t,H11; 2.24, (3H), S, 3Me; 2.08, (2H),t,H6; 1.83, (3H),S,5Me; 1.75-1.3, (8H), H7,8,910; 3.15, (2H),d of d, 1.8, (1H), m, 0.92, (6H), d,isobutyl.

The following compounds were prepared similarly:

EXAMPLE 9

(2E,4E) N-isobutyl 9-(1-naphthyloxy)-3-methylnona-2,4-dienamide (yellow oil), starting from a reaction of 1-naphthol and bromopentanol in dimethylformamide in the presence of sodium hydride, the bromopentanol having been prepared from pentanediol and hydrobromic acid.

EXAMPLE 10

(33% 2E,4E,67%2Z,4E) N-1,2-dimethylpropyl 9-(1-naphthyloxy)-3-methylnona-2,4-dienamide (yellow oil).

EXAMPLE 11

(67% 2E,4E; 33%2Z,4E)N-1,2-dimethylpropyl 9-(1-naphthyloxy)-3-methylnona-2,4-dienamide (yellow oil).

EXAMPLE 12

N-Isobutyl 11-(3',5'-bistrifluoromethylbenzyloxy)-3-ethyl-undeca-2,4-dienamide 7-(3',5'-bistrifluoromethylbenzyloxy)heptan-1-al (See Example 2, 4.97g, 13.96 mmol) was reacted with carboethoxymethylene triphenylphosphorane (4.86g, 13.96 mmol, Lancaster Synthesis Ltd., U.K.) in dry dichloromethane to give ethyl 9-(3',5'-bistrifluoromethylbenzyloxy)nona-2- enoate (5g). The ester (5g, 13.55 mmol) was reacted with diisobutylaluminium hydride (27 mmol) in toluene-dichloromethane at −30°. After conventional work-up, 9-(3',5'-bistrifluoromethylbenzyloxy)nona-2-en-1-ol (4.43g) was obtained. The alcohol was converted into 9-(3',5'-bistrifluoromethylbenzyloxy)-nona-2-en-al by Swern oxidation (oxalyl chloride-dimethylsulphoxide, see EP-A-164 187).

The above aldehyde (4.47g, 15.13 mmol) was reacted in dry ether with ethyl magnesium bromide prepared from magnesium (0.36 g, 15.13 mmol) and bromoethane (1.65 g, 15.13 mmol). After conventional work-up with ammonium chloride, the crude product was purified by chromatography (silica, ether:hexane) to give 11-(3',5'-bistrifluoromethylbenzyloxy)undeca-4-ene-3-ol which was converted by Swern oxidation into 11-(3',5'-bistrifluoromethylbenzyloxy)undeca-4-ene-3-one.

n-Butyl lithium (4.99 mmol) in hexane was added to N-isopropyl cyclohexylamine (0.69 g, 4.88 mmol, Aldrich Chem Co.) in dry tetrahydrofuran (20 ml) at −78° under nitrogen. After 15 mins, ethyl trimethylsilylacetate (0.78 g, 4.88 mmol, Fluka Chem. Co.) was added. After a further 10 mins, 11-(3',5'-bistrifluoromethylbenzyloxy) undeca-4-ene-3-one (1 g, 2.44 mmol) was added and the temperature was allowed to reach room temperature. After conventional work-up and chromatography on silica, ethyl 11-(3',5'-bistrifluoromethylbenzyloxy)-3-ethyl-undeca-2, 4- dienoate was obtained as a mixture of two isomers.

The above esters (0.8 g, 1.67 mmol) were treated with a complex prepared from isobutylamine (0.18 ml, 1.84 mmol) and trimethyl aluminium (1.84 mmol) in toluene (see Example 5). After chromatography, (2E, 4E) N-isobutyl 11-(3',5'-bistrifluoromethylbenzyloxy)-3-ethyl-undeca-2, 4-dienamide was obtained as a yellow oil. Glc, 3% OV210 at 250°, retention time 1.6 min; tlc, $R_f$ (silica-ether) 0.64; NMR: 7.81 (3H), aromatic; 6.03 (1H),m,H5; 5.92 (1H),d,H4; 5.52 (1H),s,H2; 5.45 (1H), NH; 4.62 (2H),s,benzylic; 3.52 (2H),t,H11; 2.81 (2H), q, 1.11 (3H),t, 3-Et; 2.18 (2H),m,H6; 1.3–1.7 (8H), satd.-chain; 3.23 (2H)t, 1.80 (1H),m, 0.94 (6H),d,isobutyl.

EXAMPLE 13

N-Isobutyl 11-(3',5'-bistrifluoromethylbenzyloxy)-3-fluoromethylundeca-2,4-dienamide 1-Chloro-3-fluoro-prop-2-one (16.1 g, 146 mmol, Bergmann & Cohen, *J Am. Chem Soc.*, 1958, 2259) in dichloromethane was treated with carboethoxymethylenetriphenylphosphorane (50.5 g, 146 mmol). After 48 hours at room temperature, the reaction was worked up in conventional fashion and purified by column chromatography (silica-ether hexane) to give ethyl 4-chloro-3-fluoro-methylcrotonate. The latter (18 g, 100 mmol) was added at 100° to triethylphosphite (23.3 g, 140 mmol). The mixture was warmed to 150°, maintained at that temperature for 6 hours and subjected to distillation to give triethyl 3-fluoromethyl-4-phosphonocrotonate (21 g) (bp (1 mm) 140°–50°).

The above phosphonate (3 g, 1123 mmol) was reacted with lithium diisopropylamide (11.23 mmol) and the resultant anion reacted with 7-(3',5'-bistrifluoromethylbenzyloxy)-heptan-1-al (4 g, 11.23 mmol) in dry THF (as in Example 1). After work-up and purification, ethyl 11-(3',5'-bistrifluoromethylbenzyloxy)-3-fluoromethylundeca-2,4-dienoate (3.95 g) was obtained. The ester was converted to the dienoic acid and then as in Example 1 to give ( 2E,4E) N-isobutyl 11-(3,5-bistrifluoromethylbenzyloxy)-3-fluoromethylundeca-2,4-dienamide as a yellow oil. ($R_f$, silica/ether, 0.64). NMR: 7.81 (3H),s,aromatic; 6.22 (1H),m,H; 6.05 (1H),d,H; 5.72 (1H),s,H2; 5.64 (2H),d,CH$_2$F; 5.68 (1H), NH; 4.62 (2H),s,benzylic; 3.56 (2H),t,H11; 2.29 (2H),m,H6; 1.3–1.7 (8H), saturated chain; 3.26 (2H),t,1.80 (1H),m, 0.95 (6H),d,isobutyl.

EXAMPLE 14

N-1,2-Dimethylpropyl 11-(3',5'-bistrifluoromethylbenzyloxy)-3-fluoromethyl-undeca-2,4-dienamide Prepared as in Example 13.
$R_f$(silica/ether) 0.66.

EXAMPLE 15

N-isobutyl 12-(2-naphthyloxy)-3-methyldodeca-2,4-dienamide

Prepared as in Example 5, starting from 2-naphthol and bromooctanol, the latter being prepared from octanediol and hydrobromic acid mp 84°–6°.

EXAMPLE 16

N-1-methylpropyl 12-(2-naphthyloxy)-3-methyldodeca-2,4-dienamide

Prepared as in Example 5 m.p. 65°–8°

EXAMPLE 17

N-isobutyl 11-(2',3',4',5',6'-pentafluorobenzyloxy)-3-methylundeca-2,4-dienamide Prepared as in Example 5, starting from pentafluorobenzyl bromide
$R_f$(silica/ether) 0.57.
70% (2E,4E) 30% (2Z,4Z).

EXAMPLE 18

N-1,1,2-trimethylpropyl 11-(3',5'-bistrifluoromethylbenyloxy)-3-methylundeca-2,4-dienamide Prepared as in Example 1, starting from 3,5-bis(trifluoromethyl)phenol.
$R_f$(silica/ether) 0.70.
1:1 (2E:4E): ( 2Z,4Z).

EXAMPLE 19

N-Isobutyl 11-(2',4'-dichlorobenzyloxy)-3-methylundeca-2,4-dienamide

Prepared as in Example 5.
$R_f$(silica/ether) 0.60.
75% (2E, 4E) 25% (2Z, 4E).

EXAMPLE 20

N-Isobutyl 11-(3',5'-bistrifluoromethylbenzyloxy)-3-trifluoromethyl-undeca-2,4-dienamide Cis -(E) 3-trifluoromethyl triethylphosphonocrotonate was prepared according to Liu et al (J.Am. Chem. Soc., 1982, 104,4979) and reacted with 7-(3',5'-bistrifluoromethylbenzyloxy)-heptan-1-al as in Example 2 to give an ester which was reacted with trimethyl aluminium and isobutylamine as in Example 5 to give the title compound as a yellow oil. $R_f$(silica/1:1 ether:hexane) 0.54 >98% 2-cis, 4-trans (2E, 4E).

'H NMR (olefinics): 7.19,(d,1H),H4; 6.26,(M,1H),H5; 6.16,(s,1H),H2.

The following further compounds were made by analogous routes. Sources of or references for starting materials are indicated if appropriate.

EXAMPLE 21

21 N-Isobutyl 3-methyl 11-(2'-chloro-4'-fluorobenzyloxy)undeca-2,4-dienamide.

EXAMPLE 22

N-Isobutyl 3-methyl 11-(3',5'-dichlorobenzyloxy)undeca-2,4-dienamide.

EXAMPLE 23

N-Isobutyl 3-methyl 11-(2',4'-dibromobenzyloxy)undeca-2,4-dienamide.

EXAMPLE 24

N-Isobutyl 3-methyl 11-(2',3',5',6'-tetrafluorobenzyloxy)undeca-2,4-dienamide.

EXAMPLE 25

N-Isobutyl 3-methyl 11-(4'-trifluoromethylthiobenzyloxy)undeca-2,4-dienamide.

EXAMPLE 26

N-Isobutyl 3-methyl 11-(2'-fluoro-4'-chlorobenzyloxy)undeca-2,4-dienamide.

EXAMPLE 27

N-2-methyl-prop-2-enyl 3-methyl 11-(3',5'bistrifluoromethylbenzyloxy)undeca-2,4-dienamide.

EXAMPLE 28

N-Isobutyl 2-methyl 11-(3',5'-bistrifluoromethylbenzyloxy)undeca-2,4-dienamide,

EXAMPLE 29

N-Isobutyl 4-methyl 11-(3,5'-bistrifluoromethylbenzyloxy)undeca-2,4-dienamide.

EXAMPLE 30

N-Isobutyl 3,4-dimethyl 11-(3',5'-bis-trifluoromethybenzyloxy)undeca-2,4-dienamide.

EXAMPLE 31

N-(2-methyl-1,3-dioxalan-2-yl)methyl 3-methyl 11-(1-naphthyloxy)undeca-2,4-dienamide.

EXAMPLE 32

N-Isobutyl 3-methyl 11-(1-naphthyloxy)undeca-2,4-dienamide.

EXAMPLE 33

N-Isobutyl 3-methyl 11-(2-naphthylmethoxy) undeca-2,4-dienamide.

EXAMPLE 34

N-Isobutyl 3-methyl 10-(1-naphthylmethoxy) deca-2,4-dienamide.

EXAMPLE 35 N-Isobutyl 3-methyl 11-(2',6'-dichloro-4'-trifluoromethylbenzyloxy)undeca-2,4-dienamide.

EXAMPLE 36

N-Isobutyl 3-methyl 11-(3'-chloro-4'-fluorobenzyloxy)undeca-2,4-dienamide.

EXAMPLE 37

N-Isobutyl 3-methyl 11-(4'-bromo-2'-chlorobenzyloxy)undeca-2,4-dienamide.

EXAMPLE 38

N-Isobutyl 3-methyl 11-(2',4'-bistrifluoromethylbenzyloxy)undeca-2,4-dienamide.

EXAMPLE 39

N-2-methyl-prop-2-enyl 3-methyl 11-(2',4'-bistrifluoromethylbenzyloxy)undeca-2,4-dienamide.

EXAMPLE 40

N-Isobutyl 3-methyl 11-(2',4',5'-trichlorobenzyloxy)undeca-2,4-dienamide.

EXAMPLE 41

N-Isobutyl 3-methyl 11-(2,2-difluoro-1,3-benzodioxol-5-yl)-methoxy-undeca-2,4-dienamide (A 2,2-difluoro-1,3-benzodioxol-5-yl group may be represented as:

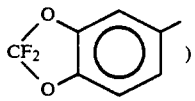 )

Examples 21 to 41 were prepared as mixtures of (2E,4E) and (2Z,4E) dienamides in which the former predominates.

Physical data for Examples 21–41

| Example No. | $R_f$ | (silica/ether) | $n_d$ | m.p. |
|---|---|---|---|---|
| 21 | 0.50 | (4:6 EtOAc/hexane) | | |
| 22 | 0.59 | | | |
| 23 | 0.52 | | | |
| 24 | 0.61 | | 1.508 | |
| 25 | 0.64 | | | 36–45° |
| 26 | 0.30 | (3:7 EtOAc/hexane) | | |
| 27 | 0.65 | | 1.495 | |
| 28 | 0.56 | | 1.483 | |
| 29 | 0.52 | | 1.488 | |
| 30 | 0.59 | | 1.486 | |
| 31 | 0.46 | | | |
| 32 | 0.70 | | | |
| 33 | 0.59 | | | |
| 34 | 0.20 | (1:1 ether/hexane) | | |
| 35 | 0.67 | | | |
| 36 | 0.40 | (1:1 ether/hexane) | | |
| 37 | 0.22 | (1:1 ether/hexane) | | |
| 38 | 0.52 | | | |
| 39 | 0.62 | | | |
| 40 | 0.65 | | | |
| 41 | 0.59 | | | |

Starting Materials for Examples 21 to 41

Alkanediols, phosphonocrotonates and amines were all as for Examples 1 to 20.

starting benzylhalides (either bromides or chlorides) for the following compounds were obtained from either Aldrich Chem.Co.Ltd., Lancaster Synthesis or Fluorochem Ltd.:

Ex. nos:- 24, 27, 28, 29, 30, 31, 32, 33, 34, 38, 39, 40.

Benzylhalides for the following were obtained by bromination of the appropriate toluene with N-bromosuccinimide:

Ex. nos:- 21, 22, 23, 25, 26, 37.

The appropriate toluenes for Examples 21, 22, & 26 were obtained from commercial sources (ex Lancaster Synthesis).

The appropriate toluene for Example 23 was prepared from 2-bromo-4-amino-toluene, obtained in turn by reduction of commercially available 2-bromo-4-nitrotoluene (ex Lancaster Synthesis).

The appropriate toluene for Example 37 was prepared by a Sandmeyer sequence from commercially available 3-chloro-4-methylaniline (ex. Aldrich).

The appropriate toluene for Example 25 was obtained by trifluoromethylation of 4-methylthiophenol (ex Aldrich) by trifluoromethyliodide in liquid ammonia/dry ether under photochemical conditions (298nm).

The following were prepared by reaction of the appropriate benzyl alcohol with phosphorous tribromide: Example Nos. 35, 41.

The alcohol for Example 35 was prepared starting from 2,6-dichloro-4-trifluoromethylaniline, in turn prepared from chlorination of 4-trifluoromethylaniline with N-chlorosuccinimide.

The alcohol for Example 41 was prepared by reduction with sodium borohydride of the appropriate aldehyde prepared by a literature method (*J.Org.Chem.*, 37, 673 (1972)).

The benzylhalide for Example 36 was prepared directly from 2-fluorochlorobenzene (ex. Lancaster Synthesis) according to the literature (*J. Org.Chem.*, 26, 2353 (1961)).

BIOLOGICAL ACTIVITY

A. Topical application versus house flies

Compounds of the invention were administered topically in Cellosolve solution, with or without 6 ug piperonyl butoxide, to adult female *Musca domestica* (WRL strain). The results, in terms of % kill, are given in Table 1.

In addition, the compounds of Examples 9–14 showed activity at <3 μg (+6 μg PB).

B. Activity versus grain pests

Approximately 20 each of *Sitophilus granarius* and *Tribolium castaneum* adults are placed in a tube of 15 g grain onto which 1.5 ml of a 0.2% w/v solution of the compound has been pipetted and left to dry. % Mortality at 7 days is given in Table 1.

TABLE 1

| Compound of Example No. | Dose (ug) | M. domestica −PB | +PB | S.g. | T.c. |
|---|---|---|---|---|---|
| 2 | 0.6 | 77.5 | 100 | 89 | 0 |
| 3 | 0.6 | 53 | 100 | — | — |
| 4 | 0.6 | 24 | — | 36 | 0 |
|   | 0.12 | — | 84 | — | — |
| 5 | 0.6 | 5 | 100 | 38 | 0 |
| 6 | 1.5 | 19 | — | — | — |
|   | 0.3 | — | 50 | — | — |
| 7 | 0.3 | — | 52 | — | — |
| 8 | 3 | 0 | 0 | 4 | 12 |

C. Activity versus blowfly

The compounds of Examples 2 and 5 had an effective dose of <c10 ppm against *Lucilia cuprina*.

D. Activity versus mosquito

Against *Culex fatigans* in a wind tunnel, the compounds of Examples 2 and 5 each had an $LC_{50}$ of <1% in OPD/dichloromethane solution.

E. Trackspray

When sprayed as an acetone:water:wetters emulsion (5:94.5:0) the following examples showed activity at <1000 ppm sprayed against:

| M. domestica: | 2, 9, 11, 12, 15, 16, 17, 19, 20 |
| C. quinquefasciatus: | 9, 11 |
| A. aegypti: | 9 |
| P. xylostella: | 2, 4, 9, 11, 12, 15, 16, 17, 19, 20 |
| M. persicae: | 2, 3, 4, 11, 12 |
| T. urticae: | 2, 3, 4, 15, 16, 17, 18, 19, 20 |

F. *Spodoptera littoralis*

The compound of Example 2 showed activity against larvae of *S. littoralis* when topically applied at 10 μg/larva.

Examples 15, 16, 17, 19, 20 showed activity against larvae of *S. littoralis* when injected at 5 μg/larva.

D. Comparative example

The compound of Example 2 was compared with the compound of Example 4 of EP-A-164 187, namely the analogue lacking the 3-methyl group. When applied as deposits on glass, the following results were obtained.

| Compound | $LC_{50}$ (mg·m$^{-2}$) A. aegypti | C. quinquefasciens |
|---|---|---|
| Ex. 2 | c40 | c40 |
| prior art analogue | >200 | >200 |

When applied as acetone solutions to *Spodoptera littoralis* larvae, Ex. 2 had $LD_{50}=2$ μg and the analogue $LD_{50}>10$ μg.

| Formulations | | |
|---|---|---|
| 1. | Emulsifiable Concentrate | |
|   | Compound of Example 1 | 10.00 |
|   | Ethylan KEO | 20.00 |
|   | Xylene | 67.50 |
|   | Butylated Hydroxyanisole | 2.50 |
|   |   | 100.00 |
| 2. | Wettable Powder | |
|   | Compound of Example 1 | 25.00 |
|   | Attapulgite | 69.50 |
|   | Sodium isopropylbenzene sulphonate | 0.50 |
|   | Sodium salt of condensed naphthalene sulphonic acid | 2.50 |
|   | Butylated Hydroxytoluene | 2.50 |
|   |   | 100.00 |
| 3. | Dust | |
|   | Compound of Example 1 | 0.50 |
|   | Butylated Hydroxyanisole | 0.10 |
|   | Talc | 99.40 |
|   |   | 100.00 |
| 4. | Bait | |
|   | Compound of Example 1 | 40.25 |
|   | Icing Sugar | 59.65 |
|   | Butylated hydroxy toluene | 0.10 |
|   |   | 100.00 |
| 5. | Lacquer | |
|   | Compound of Example 1 | 2.50 |
|   | Resin | 5.00 |
|   | Butylated Hydroxy anisole | 0.50 |
|   | High aromatic white spirit | 92.00 |
|   |   | 100.00 |
| 6. | Aerosol | |
|   | Compound of Example 1 | 0.30 |
|   | Butylated Hydroxy anisole | 0.10 |
|   | 1,1,1-Trichloroethane | 4.00 |
|   | Odourless Kerosene | 15.60 |
|   | Arcton 11/12. 50:50 mix | 80.00 |
|   |   | 100.00 |
| 7. | Spray | |
|   | Compound of Example 1 | 0.10 |
|   | Butylated Hydroxy anisole | 0.10 |
|   | Xylene | 10.00 |
|   | Odourless Kerosene | 89.80 |
|   |   | 100.00 |
| 8. | Potentiated Spray | |
|   | Compound of Example 1 | 0.10 |
|   | Permethrin | 0.50 |
|   | Butylated Hydroxyanisole | 0.10 |
|   | Xylene | 10.10 |
|   | Odourless Kerosene | 89.20 |
|   |   | 100.00 |

What we claim is:

1. A compound of Formula (I)

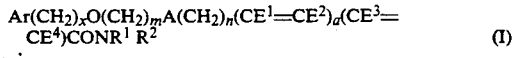

$$Ar(CH_2)_xO(CH_2)_mA(CH_2)_n(CE^1=CE^2)_a(CE^3=CE^4)CONR^1R^2 \quad (I)$$

wherein

Ar is phenyl or naphthyl, in either case optionally substituted by one of more of $C_{1-6}$ alkyl, halogen, a group $RS(O)_z$— where R is $C_{1-4}$-alkyl optionally substituted by one or more halogen and z is 0, 1 or 2, $C_{1-6}$ alkoxy, $C_{1-6}$ alkyl substituted by halo, or $C_{1-6}$ alkoxy substituted by halo, or Ar is also 2,2-difluoro-1,3-benzodioxol-5-yl,

X=1 m=1 to 7 n=1 to 7

A=$CH_2$ or oxygen a=0 or 1

$R^1$ and $R^2$ are independently selected from hydrogen, $C_{1-6}$ alkyl and $C_{3-6}$ cycloalkyl (either of which may be substituted by one or more of halogen, $C_{1-6}$ alkyl, $C_{2-6}$ alkenyl, $C_{2-6}$ alkoxy, $C_{2-6}$ alkynyl, dioxolanyl and $C_{3-6}$ cycloalkyl)

$E^1$, $E^2$, $E^3$ and $E^4$ are independently selected from hydrogen, $C_{1-4}$ alkyl optionally substituted by halogen, and nitrile, provided that at least one of $E^1$, $E^2$, $E^3$ and $E^4$ is optionally substituted alkyl or nitrile.

2. A compound according to claim 1 wherein Ar is phenyl substituted by one or more halogen or trifluoromethyl groups.

3. A compound according to claim 1 wherein a is 1.

4. A compound according to claim 1 wherein A is —CH$_2$— and the sum of m and n is equal to an odd number.

5. A compound according to claim 1 wherein $R^1$ is hydrogen and $R^2$ is $C_{1-8}$ alkyl.

6. A compound according to claim 1 wherein the stereochemistry of the or each double bond conjugated to the amide carbonyl is trans.

7. A compound according to claim 1 wherein $E^1$, $E^2$ and $E^4$ are hydrogen and $E^3$ is selected from methyl, fluoromethyl and trifluoromethyl.

8. A compound selected from the group comprising N-isobutyl 11-(3,5-bistrifluoromethylbenzyloxy)-3-methylundeca-2,4-dienamide, and N-isobutyl 11-(2, 4-dichlorobenzyloxy)-3-methylundeca-2,4-dienamide (in each case 2E, 4E).

9. A pesticidal composition comprising a pesticidally sufficient amount of a compound according to claim 1 and one or more diluents or carriers.

10. A method of combatting pests by applying to the pest or a useful locus a pesticidally sufficient amount of a compound according to claim 1.

11. N-isobutyl 11-(3,5-bistrifluoromethylbenzyloxy)-3-methylundeca-2,4-dienamide.

12. A compound selected from the group consisting of:
N-1-methylpropyl 11-(3',5'-bistrifluoromethylbenzyloxy)-3-methyl-2,4-dienamide;
N-isobutyl 12-(2-naphthyloxy)-3-methyldodeca-2,4-dienamide;
N-1-methylpropyl 12-(2-naphthyloxy)-3-methyldodeca-2,4-dienamide;
N-isobutyl 11-(4'-dichlorobenzyloxy)-3-methylundeca-2,4-dienamide;
N-isobutyl 3-methyl 11-(2',4'-bromo-2'-chlorobenzyloxy) undeca-2,4-dienamide;
N-Isobutyl 3-methyl 11-(2',4'-bistrifluoromethylbenzyloxy)undeca-2,4-dienamide; and
N-2-methyl-prop-2-enyl 3-methyl 11-(2',4'-bistrifluoromethyl-benzyloxy)undeca-2,4-dienamide.

* * * * *